(12) United States Patent
Baccelli et al.

(10) Patent No.: US 8,172,843 B2
(45) Date of Patent: *May 8, 2012

(54) VERTEBRAL FIXING SYSTEM

(75) Inventors: Christian Baccelli, Saucats (FR); Karl P. Belliard, La Membrolle sur Longuenee (FR); Keyvan Mazda, Paris (FR)

(73) Assignee: Zimmer Spine S.A.S., Bordeaux (FR)

( * ) Notice: Subject to any disclaimer, the term of this patent is extended or adjusted under 35 U.S.C. 154(b) by 516 days.

This patent is subject to a terminal disclaimer.

(21) Appl. No.: 12/375,265

(22) PCT Filed: Sep. 18, 2006

(86) PCT No.: PCT/FR2006/050898
§ 371 (c)(1),
(2), (4) Date: Mar. 9, 2009

(87) PCT Pub. No.: WO2007/036657
PCT Pub. Date: Apr. 5, 2007

(65) Prior Publication Data
US 2009/0326585 A1    Dec. 31, 2009

(30) Foreign Application Priority Data

Sep. 20, 2005  (FR) .................................... 05 09570
Feb. 22, 2006  (FR) .................................... 06 50609

(51) Int. Cl.
*A61B 17/82* (2006.01)
(52) U.S. Cl. ........... 606/74; 606/324; 606/263; 606/277
(58) Field of Classification Search ................ 606/103, 606/139, 232, 247–279, 60, 246, 74, 324; 623/13.14; 24/132 R, 132 AA, 132 WL
See application file for complete search history.

(56) References Cited

U.S. PATENT DOCUMENTS 902,040 A    10/1908    Wychoff
(Continued)

FOREIGN PATENT DOCUMENTS

DE    19716504    12/1998
(Continued)

OTHER PUBLICATIONS

Office Action issued in U.S. Appl. No. 11/996,918, mailed Feb. 14, 2011, 12 pages.

(Continued)

*Primary Examiner* — Eduardo C Robert
*Assistant Examiner* — Lynnsy Schneider
(74) *Attorney, Agent, or Firm* — Seager Tufte & Wickhem LLC

(57) ABSTRACT

A vertebral fixing system comprising a connecting part with two longitudinal elements coupled to each other at a first end and having mutually facing recesses for receiving a rod. A portion of a flexible ligature extends through orifices of the two longitudinal elements to define a loop opposite two free ends of the flexible ligature. The two longitudinal elements are engaged at a second end of the connecting part via a locking means. When the two longitudinal elements of the connecting part are locked at the second end of the connecting part, two strands of the flexible ligature are pinched between the rod and a wall of the mutually facing recesses of the two longitudinal elements of the connecting part, preventing the flexible ligature from moving in translation relative to the connecting part.

20 Claims, 5 Drawing Sheets

U.S. PATENT DOCUMENTS

| | | | |
|---|---|---|---|
| 1,346,940 A | 7/1920 | Collins | |
| 2,049,361 A | 7/1936 | Ericsson | |
| 5,030,220 A | 7/1991 | Howland | |
| 5,304,178 A * | 4/1994 | Stahurski | 606/263 |
| 5,356,412 A * | 10/1994 | Golds et al. | 606/74 |
| 5,413,576 A | 5/1995 | Rivard | |
| 5,449,361 A | 9/1995 | Preissman | |
| 5,609,634 A | 3/1997 | Voydeville | |
| 5,667,508 A | 9/1997 | Errico | |
| 5,669,917 A * | 9/1997 | Sauer et al. | 606/139 |
| 5,702,399 A | 12/1997 | Kilpeta et al. | |
| 5,720,751 A | 2/1998 | Jackson | |
| 5,935,133 A | 8/1999 | Wagner et al. | |
| 5,938,663 A | 8/1999 | Petreto | |
| 5,964,769 A | 10/1999 | Wagner et al. | |
| 6,053,921 A | 4/2000 | Wagner et al. | |
| 6,086,590 A * | 7/2000 | Margulies et al. | 606/263 |
| 6,099,527 A | 8/2000 | Hochschuler et al. | |
| 6,146,386 A | 11/2000 | Blackman et al. | |
| 6,179,838 B1 * | 1/2001 | Fiz | 606/278 |
| 6,228,096 B1 | 5/2001 | Marchand | |
| 6,241,740 B1 | 6/2001 | Davis et al. | |
| 6,277,120 B1 * | 8/2001 | Lawson | 606/263 |
| 6,309,390 B1 | 10/2001 | Le Couedic et al. | |
| 6,391,030 B1 | 5/2002 | Wagner et al. | |
| 644,751 A1 | 9/2002 | Krause et al. | |
| 6,478,798 B1 | 11/2002 | Howland | |
| 6,514,255 B1 * | 2/2003 | Ferree | 606/263 |
| 6,547,770 B2 | 4/2003 | Carlsson et al. | |
| 6,547,790 B2 | 4/2003 | Harkey, III et al. | |
| 6,569,164 B1 | 5/2003 | Assaker et al. | |
| 6,569,171 B2 | 5/2003 | DeGuillebon et al. | |
| 6,616,669 B2 | 9/2003 | Ogilvie et al. | |
| 6,656,179 B1 * | 12/2003 | Schaefer et al. | 606/267 |
| 6,656,185 B2 * | 12/2003 | Gleason et al. | 606/74 |
| 6,682,533 B1 | 1/2004 | Dinsdale et al. | |
| 6,689,140 B2 | 2/2004 | Cohen | |
| 6,746,452 B2 | 6/2004 | Tuke et al. | |
| 6,773,438 B1 | 8/2004 | Knodel et al. | |
| 6,946,000 B2 | 9/2005 | Senegas et al. | |
| 7,481,828 B2 * | 1/2009 | Mazda et al. | 606/263 |
| 7,699,874 B2 * | 4/2010 | Young | 606/250 |
| 7,959,654 B2 | 6/2011 | Mazda | |
| 2002/0116013 A1 | 8/2002 | Gleason et al. | |
| 2002/0198538 A1 | 12/2002 | Kortenbach et al. | |
| 2004/0087979 A1 | 5/2004 | Field et al. | |
| 2004/0138666 A1 | 7/2004 | Molz, IV et al. | |
| 2005/0070958 A1 | 3/2005 | Swayze et al. | |
| 2005/0085815 A1 | 4/2005 | Harms | |
| 2005/0131404 A1 | 6/2005 | Mazda et al. | |
| 2005/0154403 A1 | 7/2005 | Sauer et al. | |
| 2005/0228375 A1 * | 10/2005 | Mazda et al. | 606/61 |
| 2006/0235387 A1 | 10/2006 | Peterman | |
| 2006/0235391 A1 | 10/2006 | Sutterlin, III | |
| 2007/0088359 A1 | 4/2007 | Woods et al. | |
| 2007/0299445 A1 | 12/2007 | Shadduck et al. | |
| 2008/0033557 A1 | 2/2008 | Pasquet et al. | |
| 2008/0125780 A1 | 5/2008 | Ferree | |
| 2008/0140133 A1 | 6/2008 | Allard et al. | |
| 2008/0208256 A1 | 8/2008 | Thramann | |
| 2009/0131985 A1 | 5/2009 | Mazda et al. | |
| 2009/0138048 A1 | 5/2009 | Baccelli et al. | |

FOREIGN PATENT DOCUMENTS

| | | |
|---|---|---|
| EP | 0780096 | 6/1997 |
| EP | 1815812 | 8/2007 |
| FR | 522040 | 7/1921 |
| FR | 26156 | 9/1932 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| GB | 2269753 | 2/2004 |
| JP | 2001299770 | 10/2001 |
| WO | WO9416635 A1 | 8/1994 |
| WO | WO0207622 | 1/2002 |
| WO | WO0209604 A1 | 2/2002 |
| WO | WO0217803 A2 | 3/2002 |
| WO | WO02051326 A1 | 7/2002 |
| WO | WO02071960 A1 | 9/2002 |
| WO | WO 03007829 A1 | 1/2003 |
| WO | WO03103519 A1 | 12/2003 |
| WO | WO2004010881 A1 | 2/2004 |
| WO | WO 2005020860 A3 | 3/2005 |
| WO | WO2005120277 A1 | 12/2005 |
| WO | WO 2006106268 A3 | 10/2006 |
| WO | WO 2006106246 | 12/2006 |
| WO | WO 2007023240 A3 | 3/2007 |
| WO | WO2007034112 A1 | 3/2007 |
| WO | WO 2007036657 | 4/2007 |
| WO | WO2007099258 A2 | 9/2007 |

OTHER PUBLICATIONS

Office Action issued in U.S. Appl. No. 12/059,634, mailed Feb. 15, 2011, 14 pages.

Office Action issued in U.S. Appl. No. 12/408,592, mailed Feb. 18, 2011, 17 pages.

Notice of Allowance issued in U.S. Appl. No. 12/358,748, mailed Feb. 23, 2011, 5 pages.

European Search Report for EP 08305124.3, dated Oct. 20, 2008, 3 pages.

English Translation of International Preliminary Report for PCT/FR2006/050898 on Patentability Chapter I, dated Apr. 29, 2008, 6 pages.

English Translation of International Preliminary Report on Patentability Chapter I for PCT/FR2006/050909, dated Apr. 8, 2008, 5 pages.

English Translation of the Written Opinion of the International Search Authority for PCT/FR2006/050909, dated Apr. 2, 2008, 4 pages.

English Translation of the Written Opinion of the International Search Authority for PCT/FR2006/050898, dated Apr. 28, 2008, 5 pages.

European Search Report for EP 08305183, dated Mar. 19, 2009, 10 pages.

European Search Report for EP 08305326, dated Nov. 12, 2008, 3 pages.

European Search Report for EP 2052689, dated Apr. 15, 2008, 6 pages.

European Search Report issued in EP 08305326 on Nov. 18, 2006, 5 pages.

French Preliminary Search Report and Written Opinion for FR200650609, dated Jun. 30, 2006, 5 pages.

International Search Report for WO2009053423, dated May 19, 2009, 4 pages.

International Search Report mailed Nov. 24, 2008 for PCT/EP2008/063682, 3 pages.

International Search Report for PCT/FR2006/050909 published as WO/2007/034112, dated Jan. 24, 2007, 3 pages.

Office Action for U.S. Appl. No. 10/521,914, dated Dec. 29, 2006, 21 pages.

Office Action for U.S. Appl. No. 10/521,914, dated Mar. 19, 2008, 7 pages.

Office Action for U.S. Appl. No. 10/521,914, dated Jun. 16, 2006, 13 pages.

Office Action for U.S. Appl. No. 10/521,914, dated Jul. 30, 2007, 13 pages.

International Search Report and Written Opinion for PCT/US2009/038977, mailed Jul. 22, 2009, 13 pages.

Korean Examination report for Korean Patent Application No. 1020057001238, mailed Feb. 23, 2010, 3 pages.

French Preliminary Search Report for FR0209317, dated Apr. 9, 2003, 1 page.

French Preliminary Search Report for FR0509629 mailed Jun. 9, 2006, 2 pages.

International Search Report for FR200302307, dated Jan. 2, 2004, 2 pages.

Australian Search Report for Australian Patent Application No. 2003267529, dated Nov. 15, 2007, 2 pages.
French Preliminary Search Report FR0509570, dated Jun. 29, 2006, 2 pages.
International Search Report for PCT/FR2006/050898, dated Feb. 2, 2007, 2 pages.
Written Opinion for PCT/US2009/038977, mailed Feb. 24, 2010, 7 pages.
European Search Report for European Patent Application No. 07 301 454.0, mailed Sep. 25, 2008, 8 pages.
Office Action issued in U.S. Appl. No. 11/877,160, mailed Apr. 12, 2011, 12 pages.
Office Action issued in U.S. Appl. No. 12/059,634, mailed Jun. 22, 2011, 15 pages.
Partial European Search Report issued in European Application No. 07 301 483.9, completed Apr. 15, 2008, mailed Apr. 23, 2008, 6 pages.
European Search Report and Search Opinion issued in European Application No. 07 301 483.9, completed Apr. 15, 2008, mailed Jul. 10, 2008, 10 pages.
International Search Report and Written Opinion issued in PCT Application No. PCT/EP2008/064344, completed Jan. 16, 2009, mailed May 19, 2009, 11 pages.
International Preliminary Report on Patentability issued in International Patent Application No. PCT/EP2008/063682, Apr. 13, 2010, 8 pages.
International Preliminary Report on Patentability issued in International Patent Application No. PCT/EP2008/064344, Apr. 27, 2010, 8 pages.
International Preliminary Report on Patentability issued in International Patent Application No. PCT/US2009/038977, May 27, 2010, 12 pages.
International Search Report issued in International Patent Application No. PCT/EP2008/064344, published as WO/2008/053423, mailed May 19, 2009, 5 pages.
International Search Report and Written Opinion issued in International Patent Application No. PCT/EP2008/063682, mailed Nov. 24, 2008, 11 pages.
International Search Report and Written Opinion issued in International Patent Application No. PCT/FR2006/050909, published as WO/2007/034112, mailed Jan. 24, 2007, 10 pages.
Office Action issued in U.S. Appl. No. 12/358,748, mailed Sep. 15, 2010, 7 pages.
Office Action issued in U.S. Appl. No. 11/877,160, mailed Nov. 26, 2010, 10 pages.
European Search Report issued in European Patent Application No. EP08305124.3, Oct. 24, 2008, 4 pages.
Office Action issued in U.S. Appl. No. 11/996,918, mailed Aug. 17, 2011, 11 pages.
Notice of Allowance issued in U.S. Appl. No. 11/996,918, mailed Dec. 19, 2011, 9 pages.
Office Action issued in U.S. Appl. No. 12/408,592, mailed Sep. 22, 2011, 24 pages.
Office Action issued in U.S. Appl. No. 12/059,634, mailed Oct. 5, 2011, 12 pages.
Notice of Allowance issued in U.S. Appl. No. 11/877,160 mailed Oct. 31, 2011, 7 pages.

* cited by examiner

US 8,172,843 B2

VERTEBRAL FIXING SYSTEM

CROSS-REFERENCE TO RELATED APPLICATIONS

This application claims foreign priority benefits under 35 U.S.C. §119 to International Application No. PCT/FR2006/050898, filed Sep. 18, 2006, which claims priority to French Application Nos. FR 0650609, filed Feb. 22, 2006, and FR 0509570, filed Sep. 29, 2005. All applications listed herein are incorporated by reference in their entireties.

TECHNICAL FIELD OF THE INVENTION

The present invention relates to vertebral fixing system suitable for being mounted on a vertebra.

An intended field of application is particularly, but not exclusively, the treatment of scoliosis, or more generally correcting abnormal curvatures of the spine.

BACKGROUND OF THE RELATED ART

The spine is constituted by superposed vertebrae that are normally in alignment along a vertical axis, going from the lumbar vertebrae to the cervical vertebrae, each vertebra presenting a posterior wall from which there projects a spinous process and two sides having walls from which there project the ribs and/or transverse processes. When the spine of an individual presents abnormal curvature, the vertebrae are inclined relative to one another and relative to said vertebral axis. The sides of the vertebrae situated on one side are thus moved closer together forming a concave side, whereas the sides of the vertebrae on the other side are spaced apart from one another and form a convex side.

In order to straighten the spinal column, the sides of the vertebrae on the concave side are spaced apart from one another and moved relative to one another to distances that are substantially equivalent to those between the sides of the vertebrae on the other side. In order to keep the vertebrae in that relative positioning, known devices have screws that are inserted in the vertebrae or hooks that are inserted along the inside wall of the vertebral canal, and rods that are for interconnecting the screws or the hooks.

The hooks are generally inserted in pairs into each vertebra and on either side close to the pedicles, with their heads projecting from the posterior wall of the vertebra, one on either side of the spinous process. By way of example, the heads form a socket suitable for receiving a rod that is held in place by means of a nut screwed onto the head so as to press against the rod. The rows constituted by the heads of the hooks situated on either side of the spinous processes are interconnected and held in a fixed position by two rods that are parallel to each other and to the axis of the spine.

SUMMARY OF THE INVENTION

Nevertheless, it is difficult to use such hooks since the operator must under no circumstances interfere with the spinal cord that extends along the center of the vertebral canal, since otherwise there is a danger of paralyzing the patient.

The use of screws makes it possible to diminish the risks of the operation. The screws likewise have socket-forming heads and they are inserted in pairs into the posterior walls of the vertebrae in the pedicles on either side of the spinous process. Thus, the screws constitute points for fixing the vertebrae so as to hold them relative to one another. Nevertheless, they are necessarily introduced into the pedicles of the vertebrae, and under certain circumstances such pedicles can be small in size or damaged.

SUMMARY OF THE INVENTION

The problem that arises and that the present invention seeks to solve is how to establish fixing points when it is not possible to introduce screws into the vertebrae in the curved portion of the spine and when the use of hooks is too dangerous. PCT patent application WO 2004/010881 in the name of the Applicant describes a vertebral fixing system that enables the problem to be solved.

That vertebral fixing system adapted to be mounted on a vertebra of the spine to connect it to a rod comprises:

a connecting part placed facing said rib and/or said transverse process and suitable for being connected to said rod;

an elongate flexible ligature suitable for connecting together said connecting part and at least one rib and/or one transverse process; and adjustable locking means fastened to said connecting part, said ligature having a first end secured to said connecting part and a free second end suitable for sliding in said connecting part to form a loop, said locking means being suitable for holding in a fixed position both said connecting part relative to said rod, and a length of said ligature between said ends that is suitable for being prevented from moving in translation relative to said connecting part by said adjustable locking means, whereby the loop presents a length that is determined so as to prevent relative displacement of said rod and said vertebra in opposite directions.

That system is satisfactory, but under certain circumstances it can present the following drawback. When the surgeon exerts traction on the free end of the flexible ligature, the ligature can be jammed by friction against the bottom face of the process. Under such circumstances, it will be understood that although the length of the ligature between the bottom face of the process and the zone where traction is applied to the ligature is indeed under tension, the length that extends between the end of the ligature that is secured to the elongate passageway and the bottom face of the process is not under tension. Thus, overall, the ligature does not perform its function of fastening to the vertebra in appropriate manner.

An object of the present invention is to provide a vertebral fixing system that enables the above-mentioned drawbacks to be avoided and that provides controlled locking of the ligature.

According to the invention, to achieve this object, the vertebral fixing system suitable for being mounted on a vertebra of the spine in order to connect it to a rod comprises:

a connecting part presenting first and second sides and suitable for being connected to said rod;

a flexible ligature of elongate shape suitable for connecting together said connecting part and at least one rib and/or transverse process and/or a portion of the posterior arc of a vertebra; and adjustable locking means mounted on said connecting part; and said system is characterized in that:

said ligature presents two free ends;

said connecting part defines at least one passageway for passing said ligature in such a manner that two distinct strands of said ligature can be engaged in said passageway(s) so that said two ligature strands define a first ligature portion forming a loop that extends from a first side of said connecting part, and second and third ligature portions extending from the other side of said connecting part between respective ones of said ligature strands and said free ends; and said locking means are distinct from the connecting part and co-operate therewith by screw-fastening, said locking means being capable of taking a first position relative to the connecting part in which the two ligature strands are free in said strand-passing passageway(s), a second position relative to the connecting part in which the two ligature strands are prevented from moving in translation relative to the connecting part, and intermediate positions in which a coefficient of friction is created between said ligature strands and said connecting part.

It will be understood that because the two ligature strands that are on either side of the transverse process are both placed in one or more passageways, when the locking means are brought into their locking position, both ligature strands can be used to exert the tension needed for fixing to the vertebra by means of a rib and/or a portion of the posterior arc of a vertebra and/or a transverse process.

In addition, since the locking means co-operate with the connecting part by screw-fastening, the "dimensions" of the passageways can be defined accurately during the various stages of clamping and then locking the ligature.

Preferably, the connecting part defines a single passageway and both ligature strands are engaged in the single passageway.

Also preferably, the single passageway is defined firstly by the outside surface of the portion of the rod that is engaged in the connecting part and secondly by a wall of the connecting part, and the locking means are suitable for modifying the section of the passageway.

When the locking means are in their second position, this ensures effective clamping of the two ligature strands, thereby preventing them from moving.

In a first embodiment, the connecting part comprises two longitudinal elements having first ends that are hinged together, each of said longitudinal elements presenting a recess suitable for receiving a portion of a section of said rod, a wall of said recess co-operating with the side surface of said rod to define said passageway for passing said ligature strands, said locking means being mounted at the two second ends of said longitudinal elements.

In a second embodiment, the connecting part comprises a part that is generally U-shaped, suitable for receiving said rod, and having the outer ends of the limbs of the U-shape threaded, and the adjustable locking means comprise a tapped ring suitable for co-operating with the thread on the U-shaped part, tightening the ring causing the limbs of the part to be clamped against the rod.

Preferably, said passageway(s) is/are constituted by the space between the inside wall of the recess formed in said connecting part and the side wall of said rod.

BRIEF DESCRIPTION OF THE DRAWINGS

Other characteristics and advantages of the invention appear better on reading the following description of embodiments of the invention given by way of non-limiting example. The description refers to the accompanying figures, in which.

DETAILED DESCRIPTION

Figure 1:
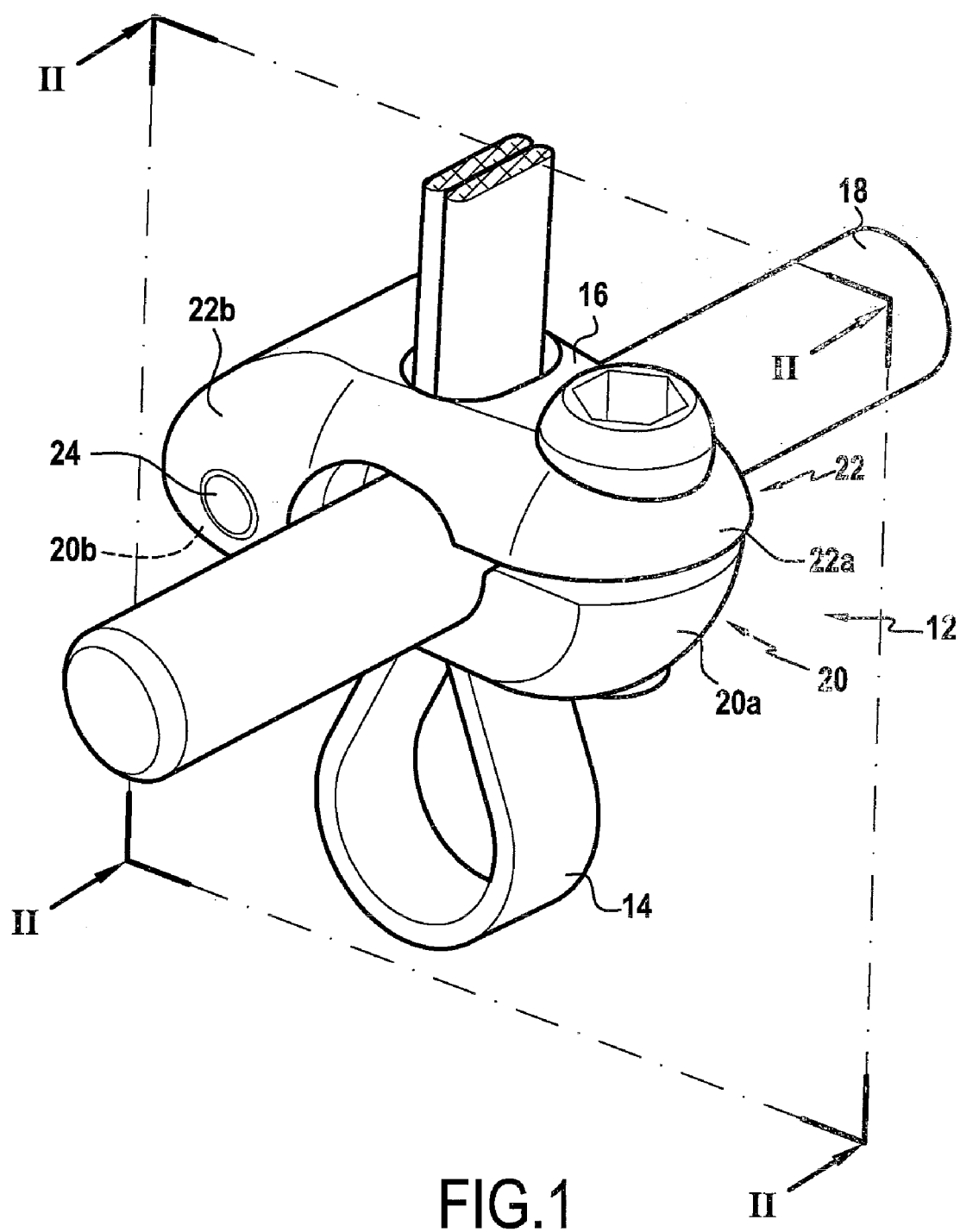
FIG. 1 is a perspective view of a first embodiment of a vertebral fixing system.

As shown in FIG. 1, in the first embodiment, the vertebral fixing system comprises a connecting part 12, a flexible ligature 14, and adjustable locking means 16. The flexible ligature 14 is of elongate shape and is capable of matching the outline of the parts it is to connect together. In this figure, there can also be seen the rod 18 that is to be secured to the vertebra by means of the vertebral fixing system. In the first embodiment, the connecting part 12 is constituted by two longitudinal elements given respective references 20 and 22, each having a first end 22a, 20a and a second end 22b, 20b.

Figure 2C:
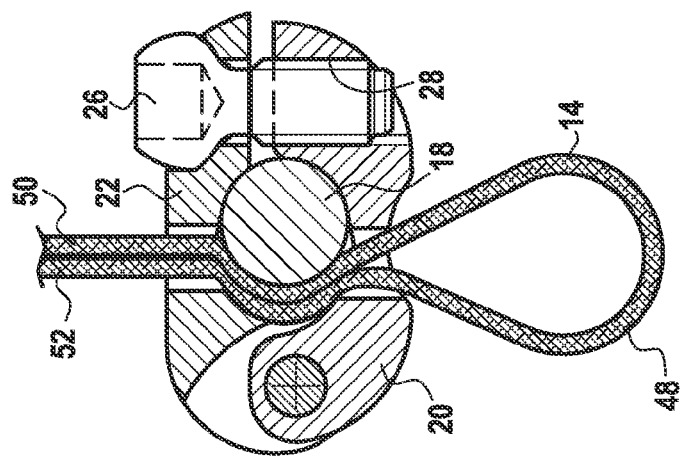
FIGS. 2A, 2B, and 2C are vertical section views of the fixing system showing the use of said system as shown in FIG. 1.
Figure 2B:
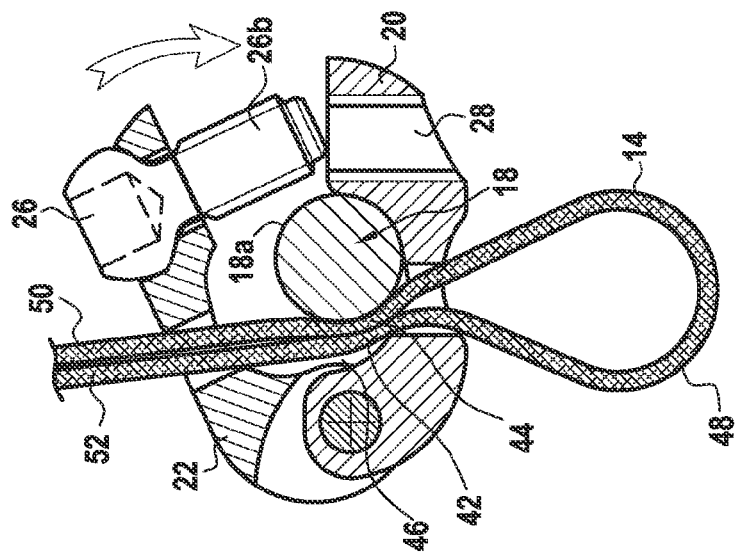
Figure 2A:
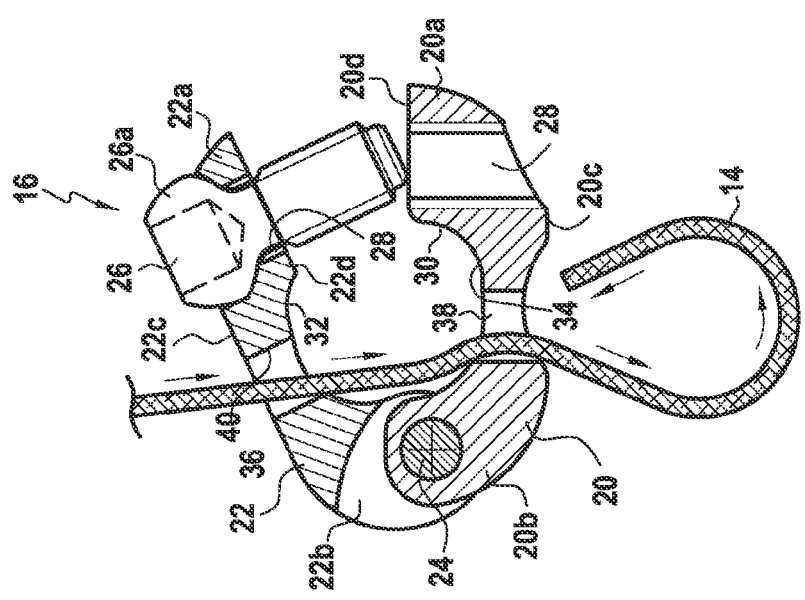

As can be seen better in FIG. 2A, the longitudinal elements 20 and 22 are hinged to each other at their second ends 20b, 22b about a pivot pin 24.

In the embodiment described, the locking means are constituted by a screw 26 having a head 26a that is engaged in a bore 28 formed in the first end 22a of the longitudinal element 22. The first end 20a of the longitudinal element 20 is pierced by a tapped bore 28 for co-operating with the threaded shank 26b of the screw 26. Each longitudinal element 20, 22 has an outside face 20c, 22c and an inside face 20d, 22d. The longitudinal elements 20 and 22 are mounted in such a manner that the inside faces 20d, 22d of the longitudinal elements face each other. The inside faces 20d, 22d of the longitudinal elements 20 and 22 have respective mutually-facing recesses 30 and 32, each of substantially semicylindrical shape. The recesses 30 and 32 define walls 34 and 36 which are ruled surfaces having generator lines parallel to the pivot axis 24. Finally, slots 38 and 40 cause the bottoms of the recesses 30 and 32 to communicate with the outside faces 20c and 22c of the longitudinal elements 20 and 22. As explained in greater detail below, the recesses 30 and 32 are for receiving the rod 18 together with a strand of the ligature 14, the slots 38 and 40 serving to pass the ligature 14.

With reference to FIGS. 2A to 2C, there follows an explanation of how the fixing system is used.

In FIG. 2A, there can be seen the longitudinal elements 20 and 22 in the spaced-apart position, a position in which the locking means 16 are naturally not active, the threaded shank 26b of the screw 26 not being engaged in the bore 28. The ligature 14 is engaged in the slots 38 and 40 of the longitudinal elements against one portion of the inside wall 34, 36 of the recesses 30 and 32. The rod 18 is then introduced into the recess 30 of the longitudinal element 20 so that the two strands 42 and 44 of the ligature 14 are disposed between the inside wall of the recesses 30 and 32 and the side face 18a of the rod 18. These two surfaces define a passageway 46 for passing the ligature 14 and having the strands 42 and 44 of the ligature 14 placed therein.

As shown better in FIG. 2B, the strands 42 and 44 of the ligature define a portion of the ligature 14 that forms a loop 48 that extends beyond the outside face 20c of the longitudinal element 20, and also two free portions 50 and 52 that extend beyond the outside face 22c of the longitudinal element 22.

When the longitudinal elements 20 and 22 are spaced apart as shown in FIG. 2B, the ligature 14 can slide freely along the passageway 46. Once the portion 48 of the ligature 14 forming the loop is placed around the transverse process or a rib or indeed a portion of the posterior arc of a vertebra, the surgeon engages the threaded shank 26b of the screw 26 in the tapped bore 28, causing the longitudinal element 22 to come progressively closer to the longitudinal element 20. This approach simultaneously reduces the section of the passageway 46 in which the strands 42 and 44 of the ligature are engaged and simultaneously introduces a certain coefficient of friction between the ligature and respectively the rod 18 and the walls of the recesses 30 and 32. Nevertheless, it is still possible for the surgeon to extract traction on the free ends 50 and 52 of the ligature 14 until sufficient tension is obtained in the ligature around the vertebral process. Once the tension in the ligature is sufficient for providing appropriate fastening, the surgeon finishes off tightening the screw 26 in the tapped bore 28, thus locking the longitudinal elements 20 and 22 together. Simultaneously, it will readily be understood that the strands 42 and 44 of the ligature are pinched between the rod 18 and the wall of the recesses 30 and 32.

In this locking position, the rod 18 is thus secured to the ligature 14 via the connecting part 12.

It will also be understood that because the surgeon exerts traction only on the free ends 50 and 52 of the ligature 14, there is no risk of jamming between the ligature 14 and the bottom face of the transverse process or of the rib, thus guaranteeing that effective fastening is provided with the transverse process or the rib or indeed a portion of the posterior arc of a vertebra.

Figure 3:
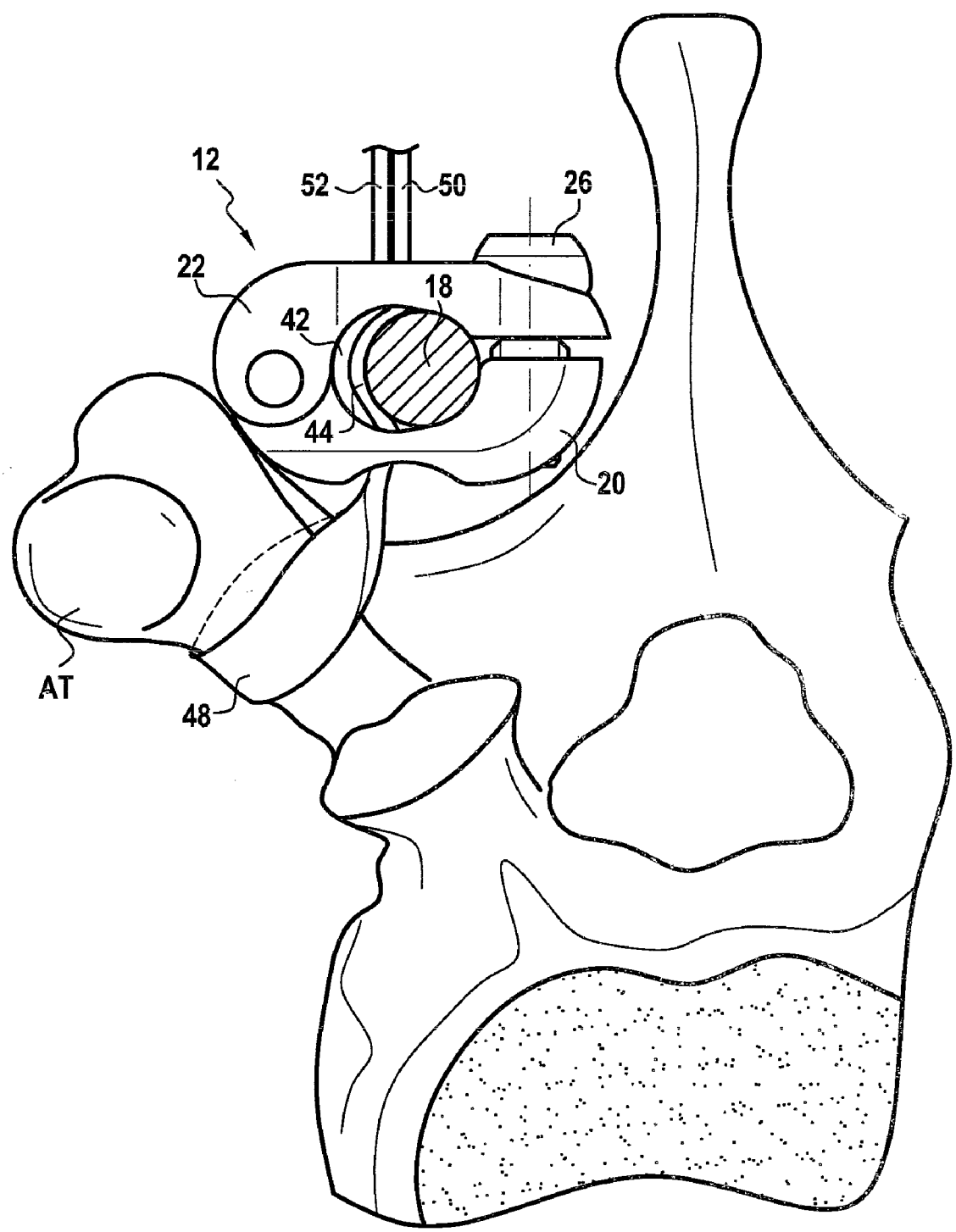
FIG. 3 is a face view showing the FIG. 1 fixing system put into place on a vertebra.
Figure 4:
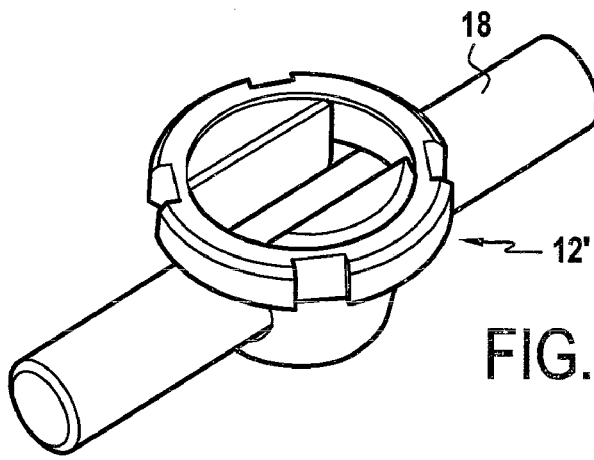
FIG. 4 is a perspective view of a second embodiment of the fixing system, the ligature not being shown.
Figure 5:
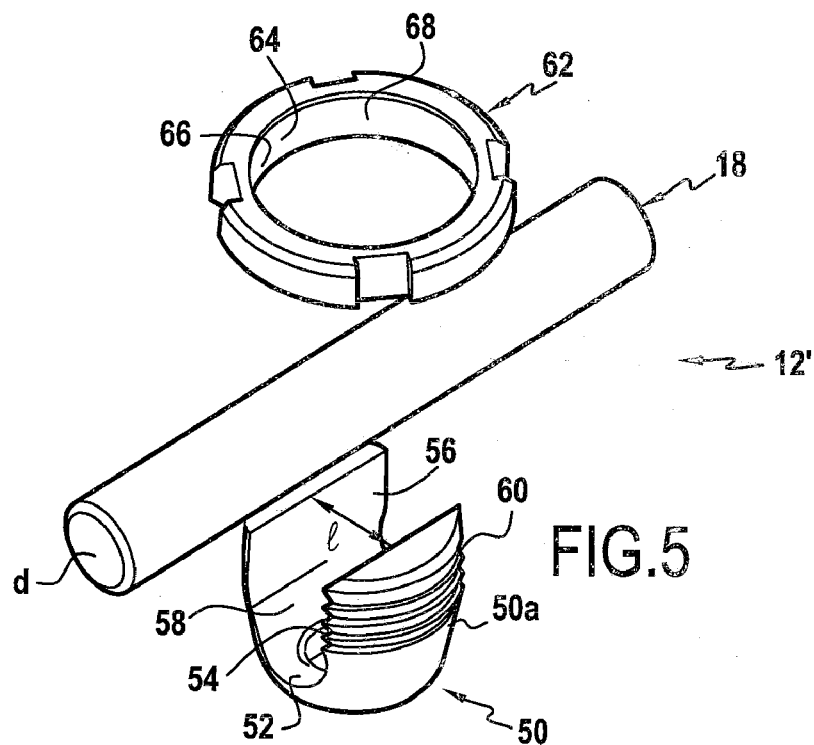
FIG. 5 is an exploded view of the connection device of FIG. 4.

This is shown in FIG. 3, where reference AT identifies the transverse process.

In the above description, both of the strands 42 and 44 of the ligature are disposed in the recesses 30 and 32 on the same side of the rod 18. This disposition serves to obtain an optimum result. Nevertheless, it would not go beyond the invention if the strands 42 and 44 of the ligature 14 were to be placed on opposite sides of the rod 18. Under such circumstances, it should be considered that the outside face 18a of the rod 18 and the inside walls of the recesses 30 and 32 define two passageways, respectively for passing each of the strands 42 and 44 of the ligature 14.

FIGS. 4 to 7B show a second embodiment of the fixing system.

In these figures, there can be seen the rod 18, the connecting part now referenced 12', and the flexible ligature 14.

In this embodiment, the connecting part 12' is constituted by a part 50 that is generally U-shaped. The inside wall of this part is constituted by a bottom 52 of substantially semicylindrical shape and by two substantially plane portions 54 and 56 that correspond to the two limbs of the part 50. The width l of the recess 58 formed in the part 50 is substantially equal to the diameter d of the rod 18. On its outside face 50a which is circularly symmetrical about a longitudinal axis of the part 50, there is provided a thread 60 occupying its upper portion. The thread 60 is located entirely above the rod 18 when it is put into place in the recess 58. The thread 60 is designed to co-operate with a clamping ring 62 that constitutes the adjustable locking means. This ring has a slightly frustoconical bore 64 with an inside face 66 that carries tapping 68.

It can thus be understood that when the ring 62 is screwed tight on the threaded portion 60 of the part 50, it deforms the limbs of the part 50 elastically, thereby pinching and clamping strands of the ligature 14 between the rod 18 and the inside wall(s) of the recess 58, in a manner explained below.

Figure 6A:
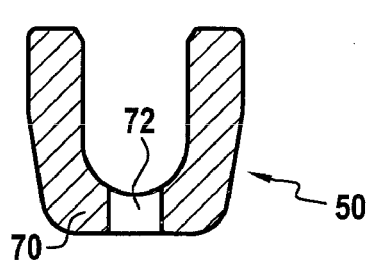
FIG. 6A is a section view on line AA of FIG. 6.
Figure 6:
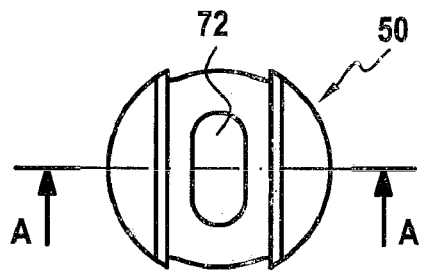
FIG. 6 is a plan view of a portion of the FIG. 1 connection device.

As shown better in FIGS. 6 and 6A, the part 50 includes in its bottom 70 a passage 72 for passing the ligature 14 in a manner explained below.

Figure 7:
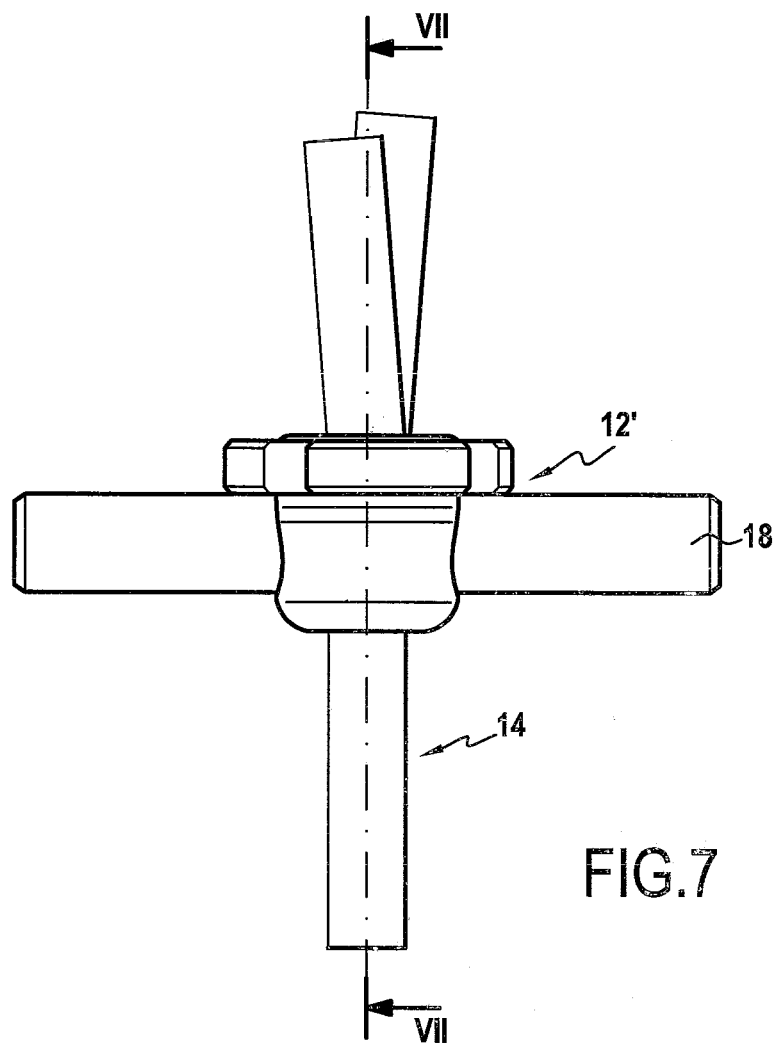
FIG. 7 is a face view of the fixing system of the second embodiment.
Figure 7A:
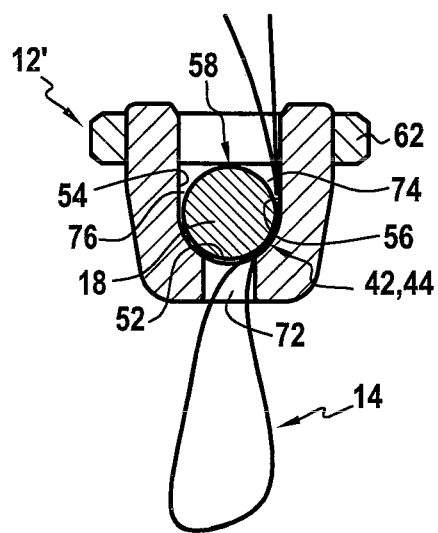
FIGS. 7A and 7B are section views on line VII-VII of FIG. 7 showing two ways in which the flexible ligature can be put into place.
Figure 7B:
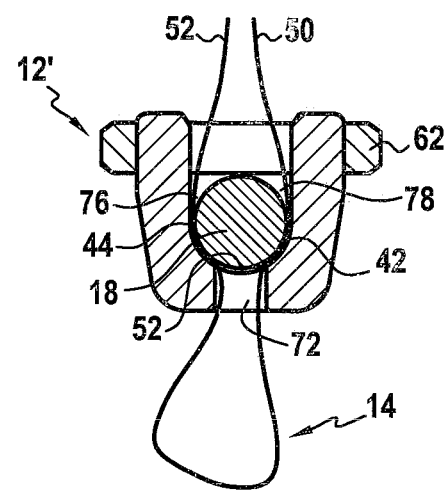

With reference to FIGS. 7, 7A, and 7B, there follows a description of two different ways of putting the flexible ligature 14 into place inside the connecting part 12' in the second embodiment. The side wall of the rod 18 and the inside wall of the recess 58 of the part 50 potentially define two passageways 74 and 76 for passing the middle strands of the flexible ligature 14. In the configuration shown in FIG. 7A, only the passageway 74 is used. Thus, both intermediate strands 42 and 44 of the flexible ligature 14 are disposed in the passage 74. This disposition presents all of the advantages described with reference to the first embodiment.

In the configuration shown in FIG. 7B, the middle strands 42 and 44 of the flexible ligature 14 are disposed respectively one in each of the passageways 76 and 78, i.e. on either side of the rod 18. This configuration likewise presents all of the advantages described with reference to the first embodiment of the device since the free ends 50 and 52 of the ligature 14 are accessible for exerting the desired traction in order to obtain suitable clamping on the spinous process prior to locking the clamping ring 62 on the part 52.

This second embodiment presents the advantage of being simpler in design since it serves in particular to avoid making two longitudinal parts constituting a kind of clamp hinged on the pin 24.

It will be understood that in both embodiments, the locking means are constituted by an element that is distinct from the connecting part and that is removable therefrom. In addition, in both cases, the locking means co-operate with the connecting part by screw engagement. It is thus possible to adjust accurately the dimensions of the ligature-passing passageway(s) as defined by the connecting part and the rod. In an initial stage, the coefficient of friction between the coefficient of the ligature and secondly the rod and the connecting part can be adjusted. In the final stage, very effective clamping of the ligature is obtained between the rod and the locking part.

The invention claimed is:

1. A vertebral fixing system, comprising:
 a connecting part having two longitudinal elements, wherein the two longitudinal elements are hinged to each other at a first end of the connecting part, wherein the two longitudinal elements comprise mutually facing recesses for receiving a rod there-between, and wherein each of the two longitudinal elements of the connecting part has an orifice;
 a flexible ligature with two free ends, wherein a portion of the flexible ligature extends through the orifices of the two longitudinal elements of the connecting part to define a loop opposite the two free ends; and
 a locking means for locking the two longitudinal elements of the connecting part at a second end of the connecting part, wherein when the two longitudinal elements of the connecting part are locked at the second end of the connecting part, two strands of the flexible ligature are pinched between the rod and a wall of the mutually facing recesses of the two longitudinal elements of the connecting part, preventing the flexible ligature from moving in translation relative to the connecting part.

2. A vertebral fixing system according to claim 1, wherein the orifices of the two longitudinal elements are in communication with the mutually facing recesses of the two longitudinal elements.

3. A vertebral fixing system according to claim 1, wherein the orifices of the two longitudinal elements, in conjunction with a portion of the mutually facing recesses of the two longitudinal elements, define a single passage way through which the flexible ligature is engaged with the connecting part.

4. A vertebral fixing system according to claim 1, wherein when the two longitudinal elements of the connecting part are not locked at the second end of the connecting part, the two strands of the flexible ligature are slidable along a single passageway.

5. A vertebral fixing system according to claim 1, wherein each of the mutually facing recesses is of substantially semi-cylindrical shape.

6. A vertebral fixing system according to claim 1, wherein at least one of the mutually facing recesses comprises a ruled surface.

7. A vertebral fixing system according to claim 1, wherein the two longitudinal elements are hinged to each other about a pivot pin.

8. A vertebral fixing system according to claim 1, wherein the locking means comprises a head that is engaged in a bore formed in one of the two longitudinal elements.

9. A vertebral fixing method, comprising:
manipulating a portion of a flexible ligature through orifices of two longitudinal elements of a connecting part to form a loop opposite two free ends of the flexible ligature;
introducing a rod into mutually facing recesses of the two longitudinal elements of the connecting part, wherein two strands of the flexible ligature are disposed between a side face of the rod and a wall of the mutually facing recesses of the two longitudinal elements of the connecting part;
engaging the two longitudinal elements of the connecting part;
tensioning the flexible ligature by pulling on the two free ends of the flexible ligature relative to the connecting part; and
locking the two longitudinal elements of the connecting part to prevent the flexible ligature from moving in translation relative to the connecting part.

10. A vertebral fixing method according to claim 9, wherein when the two longitudinal elements of the connecting part are locked at a second end of the connecting part, the two strands of the flexible ligature are pinched between the side face of the rod and the wall of the mutually facing recesses of the two longitudinal elements of the connecting part.

11. A vertebral fixing method according to claim 9, further comprising placing the loop around a bony element.

12. A vertebral fixing method according to claim 9, wherein tensioning the flexible ligature causes the loop to tighten around a bony element.

13. A vertebral fixing method according to claim 9, wherein the two longitudinal elements are coupled to each other at a first end of the connecting part.

14. A vertebral fixing method according to claim 13, wherein engaging the two longitudinal elements of the connecting part further comprises engaging the two longitudinal elements of the connecting part with a locking means at a second end of the connecting part.

15. A vertebral fixing method according to claim 14, wherein locking the two longitudinal elements of the connecting part further comprises locking the two longitudinal elements of the connecting part at the second end of the connecting part utilizing the locking means.

16. A vertebral fixing method according to claim 15, wherein the locking means comprises a head that is engaged in a bore formed in one of the two longitudinal elements.

17. A vertebral fixing method according to claim 13, wherein engaging the two longitudinal elements of the connecting part further comprises causing ends of the two longitudinal elements of the connecting part to come progressively closer to each other.

18. A vertebral fixing method according to claim 17, wherein causing the ends of the two longitudinal elements of the connecting part to come progressively closer to each other simultaneously introduces a certain coefficient of friction between the ligature and respectively the rod and the wall of the mutually facing recesses of the two longitudinal elements of the connecting part.

19. A vertebral fixing method according to claim 9, wherein prior to the locking step, the flexible ligature is slidable relative to the connecting part.

20. A vertebral fixing method, comprising:
manipulating a portion of a flexible ligature through orifices of two longitudinal elements of a connecting part to form a loop opposite two free ends of the flexible ligature, wherein the loop is placed around a bony element, and wherein the two longitudinal elements are coupled to each other at a first end of the connecting part;
introducing a rod into mutually facing recesses of the two longitudinal elements of the connecting part, wherein two strands of the flexible ligature are disposed between a side face of the rod and a wall of the mutually facing recesses of the two longitudinal elements of the connecting part;
engaging the two longitudinal elements of the connecting part at a second end of the connecting part;
tensioning the flexible ligature to fasten the loop around the bony element; and
locking the two longitudinal elements of the connecting part at the second end of the connecting part, thereby pinching the two strands of the flexible ligature between the side face of the rod and the wall of the mutually facing recesses of the two longitudinal elements of the connecting part.

* * * * *